United States Patent
Kohri et al.

(10) Patent No.: US 10,253,262 B2
(45) Date of Patent: Apr. 9, 2019

(54) FLAME RETARDANT RESIN COMPOSITION, AND CABLE AND OPTICAL FIBER CABLE USING THE SAME

(71) Applicant: FUJIKURA LTD., Tokyo (JP)

(72) Inventors: Haruka Kohri, Chiba (JP); Shoichiro Nakamura, Chiba (JP); Tomohisa Watanabe, Chiba (JP)

(73) Assignee: FUJIKURA LTD., Tokyo (JP)

( * ) Notice: Subject to any disclaimer, the term of this patent is extended or adjusted under 35 U.S.C. 154(b) by 0 days.

(21) Appl. No.: 15/528,402

(22) PCT Filed: Nov. 20, 2015

(86) PCT No.: PCT/JP2015/082659
§ 371 (c)(1),
(2) Date: May 19, 2017

(87) PCT Pub. No.: WO2016/080511
PCT Pub. Date: May 26, 2016

(65) Prior Publication Data
US 2017/0335198 A1 Nov. 23, 2017

(30) Foreign Application Priority Data

Nov. 21, 2014 (JP) .................. 2014-236117

(51) Int. Cl.
*C09K 21/14* (2006.01)
*C08K 3/22* (2006.01)
(Continued)

(52) U.S. Cl.
CPC ............... *C09K 21/14* (2013.01); *C01F 7/02* (2013.01); *C01F 11/18* (2013.01); *C08F 10/00* (2013.01);
(Continued)

(58) Field of Classification Search
CPC ... H02B 3/44; H02B 7/02; H02B 7/04; H02B 7/06; H02B 7/295; C08L 23/04;
(Continued)

(56) References Cited

U.S. PATENT DOCUMENTS

| 4,575,184 A * | 3/1986 | Ueno ................... G02B 6/4416 |
| | | 106/18.11 |
| 6,429,246 B1 * | 8/2002 | Rous ....................... C08L 23/06 |
| | | 524/261 |

(Continued)

FOREIGN PATENT DOCUMENTS

| CN | 101472983 A | 7/2009 |
| CN | 103748176 A | 4/2014 |

(Continued)

OTHER PUBLICATIONS

Supplementary European Search Report issued in corresponding European Application No. 15860294.6 dated Jun. 20, 2018 (7 pages).

(Continued)

*Primary Examiner* — William H Mayo, III
(74) *Attorney, Agent, or Firm* — Osha Liang LLP (57) ABSTRACT

A flame retardant resin composition comprises a polyolefin resin, calcium carbonate particles blended at a ratio of 5 pts. mass to 80 pts. mass, aluminum hydroxide blended at a ratio of 50 pts. mass to 125 pts. mass, a silicone-based compound blended at a ratio of more than 1 pt. mass and 10 pts. mass or less, a fatty acid-containing compound blended at a ratio of 3 pts. mass to 20 pts. mass, and a zinc-containing inorganic compound blended at a ratio of 1 pt. mass to 7 pts. mass, all relative to 100 pts. mass of the polyolefin resin. In the flame retardant resin composition, the calcium carbonate (Continued)

particles and the aluminum hydroxide are blended in total at a ratio of 55 pts. mass to 130 pts. mass relative to 100 pts. mass of the polyolefin resin.

14 Claims, 3 Drawing Sheets

(51) Int. Cl.

| | |
|---|---|
| C08K 3/26 | (2006.01) |
| C08K 3/38 | (2006.01) |
| C08K 5/09 | (2006.01) |
| C08L 23/00 | (2006.01) |
| C08L 83/04 | (2006.01) |
| G02B 6/44 | (2006.01) |
| H01B 3/44 | (2006.01) |
| H01B 7/02 | (2006.01) |
| H01B 7/17 | (2006.01) |
| H01B 7/295 | (2006.01) |
| H01B 11/22 | (2006.01) |
| C01F 7/02 | (2006.01) |
| C01F 11/18 | (2006.01) |
| C08F 10/00 | (2006.01) |
| C11C 3/00 | (2006.01) |
| C09K 21/02 | (2006.01) |
| C01G 9/00 | (2006.01) |
| C07C 53/128 | (2006.01) |

(52) U.S. Cl.
CPC ............... *C08K 3/22* (2013.01); *C08K 3/26* (2013.01); *C08K 3/38* (2013.01); *C08K 5/09* (2013.01); *C08L 23/00* (2013.01); *C08L 83/04* (2013.01); *C09K 21/02* (2013.01); *C11C 3/00* (2013.01); *G02B 6/44* (2013.01); *H01B 3/44* (2013.01); *H01B 7/02* (2013.01); *H01B 7/17* (2013.01); *H01B 7/295* (2013.01); *H01B 11/22* (2013.01); *C01G 9/00* (2013.01); *C07C 53/128* (2013.01)

(58) Field of Classification Search
CPC ... C08L 51/06; C08K 3/22; C08K 3/26; C08F 7/02; C08F 11/08; C08F 10/00

USPC ............... 174/110 R, 110 SC, 113 R, 120 R, 174/120 SC, 121 R, 121 SC
See application file for complete search history.

(56) References Cited

U.S. PATENT DOCUMENTS

| | | | | |
|---|---|---|---|---|
| 7,049,524 | B2* | 5/2006 | Belli | H01B 3/441 |
| | | | | 174/120 R |
| 8,206,825 | B2* | 6/2012 | Appel | C08L 23/08 |
| | | | | 174/110 PM |
| 2006/0237215 | A1* | 10/2006 | Alexander | H01B 3/12 |
| | | | | 174/110 R |
| 2008/0105454 | A1* | 5/2008 | Morioka | H01B 3/441 |
| | | | | 174/120 SR |
| 2009/0099289 | A1 | 4/2009 | Alexander | |
| 2013/0306350 | A1* | 11/2013 | Dinkelmeyer | H01B 7/295 |
| | | | | 174/113 R |
| 2014/0234621 | A1* | 8/2014 | Iwata | H01B 7/295 |
| | | | | 428/391 |

FOREIGN PATENT DOCUMENTS

| | | | | |
|---|---|---|---|---|
| EP | 1 164 164 A | * | 12/2001 | ............ C08K 13/02 |
| EP | 2772516 A1 | | 9/2014 | |
| EP | 3098261 A1 | | 11/2016 | |
| JP | H07-45602 B2 | | 5/1995 | |
| JP | 2001-348466 A | | 12/2001 | |
| JP | 2002-284935 A | | 10/2002 | |
| JP | 2004-189897 A | * | 7/2004 | ............ C09J 67/00 |
| JP | 2005-213480 A | * | 8/2005 | ............ C08L 23/04 |
| JP | 4879635 B2 | | 2/2012 | |
| JP | 5167428 | * | 12/2012 | ............ H01B 7/295 |
| JP | 2013-108053 A | | 6/2013 | |
| JP | 2014-094969 A | | 5/2014 | |
| JP | 2014-169389 A | | 9/2014 | |
| WO | WO2006/004698 | * | 1/2006 | ............ C08L 83/04 |
| WO | 2015/111309 A1 | | 7/2015 | |

OTHER PUBLICATIONS

Office Action issued in corresponding Chinese Patent Application No. 201580047479.7, dated Jan. 2, 2019 (18 pages).

* cited by examiner

FLAME RETARDANT RESIN COMPOSITION, AND CABLE AND OPTICAL FIBER CABLE USING THE SAME

TECHNICAL FIELD

The present invention relates to a flame retardant resin composition, and a cable and an optical fiber cable using the same.

BACKGROUND ART

As a flame retardant resin composition which can secure excellent flame retardancy while securing excellent mechanical characteristics, a flame retardant resin composition which is obtained by adding, to a polyolefin resin, a silicone-based compound such as silicone oil or magnesium stearate as a flame retardant aid together with addition of calcium carbonate with average particle diameter of 1.2 μm or more as a flame retardant is known (see, the following Patent Document 1).

CITATION LIST

Patent Document

Patent Document 1: JP 2014-94969 A.

SUMMARY OF THE INVENTION

Problem to be Solved by the Invention

The flame retardant resin composition described in the above Patent Document 1 has flame retardancy which can just pass the vertical test for a single wire based on JIS C3665-1. The vertical test for a single wire is a test in which, when a cable using the above-mentioned flame retardant resin composition as an insulating layer is prepared first, the above-mentioned cable is subsequently ignited in a vertically-hung state, and degree of fire propagation on the cable is measured, cables showing the fire propagation at certain degree or lower are graded as a pass. However, in many cases, a cable is generally laid such that plural cables are laid together, that is, multiple-line laying is carried out. In the case in which such cables laid in multiple-line catch fire, very large amount of heat is generated due to an interaction between them. For this reason, even for a cable using the flame retardant resin composition which passes the vertical test for a single wire, fire propagation occurs in some cases, and thus it was found that it cannot be said to have sufficient flame retardancy.

For this reason, there is a need for a flame retardant resin composition which can secure excellent flame retardancy while securing excellent mechanical characteristics.

The present invention has been made in view of the circumstances described above, and an object thereof is to provide a flame retardant resin composition which can secure excellent flame retardancy while securing excellent mechanical characteristics, and a cable and an optical fiber cable using the same.

Means for Solving Problem

In order to solve the above problem, the inventors of the present invention carried out various studies. As a result, the inventors of the present invention found that, when the flame retardant resin composition described in the above Patent Document 1 is blended with aluminum hydroxide and a zinc-containing inorganic compound at a predetermined ratio, the obtained flame retardant resin composition can secure more excellent flame retardancy while securing excellent mechanical characteristics. Thus, the inventors of the present invention completed the present invention.

Namely, the present invention is a flame retardant resin composition comprising a polyolefin resin, calcium carbonate particles blended at a ratio of 5 parts by mass or more and 80 parts by mass or less relative to 100 parts by mass of the polyolefin resin, aluminum hydroxide blended at a ratio of 50 parts by mass or more and 125 parts by mass or less relative to 100 parts by mass of the polyolefin resin, a silicone-based compound blended at a ratio of more than 1 part by mass and 10 parts or less by mass relative to 100 parts by mass of the polyolefin resin, a fatty acid-containing compound blended at a ratio of 3 parts by mass or more and 20 parts by mass or less relative to 100 parts by mass of the polyolefin resin, and a zinc-containing inorganic compound blended at a ratio of 1 part by mass or more and 7 parts by mass or less relative to 100 parts by mass of the polyolefin resin, in which the calcium carbonate particles and aluminum hydroxide are blended in total at a ratio of 55 parts by mass or more and 130 parts by mass or less relative to 100 parts by mass of the polyolefin resin.

According to the flame retardant resin composition of the present invention, excellent flame retardancy can be secured while excellent mechanical characteristics are secured.

Incidentally, the inventors of the present invention assume that the reason why more excellent flame retardancy can be obtained with the flame retardant resin composition of the present invention is as follows.

That is, by using calcium carbonate particles, a silicone-based compound, and a fatty acid-containing compound, a barrier layer is formed on a resin surface at the time of combustion and fire propagation can be hindered. Furthermore, since aluminum hydroxide causes a dehydrating endothermic reaction at the time of the initial combustion, the amount of heat can be suppressed even in the case of multiple-line laying, and ignition on the flame retardant resin composition or continuous combustion can be suppressed. Furthermore, the inventors of the present invention consider that the zinc-containing inorganic compound has an effect of promoting the dehydrating endothermic reaction of aluminum hydroxide. It is considered that the flame retardant effect is probably enhanced by a synergistic effect between the dehydrating endothermic reaction at the time of the initial combustion and the formation of the barrier layer preventing fire propagation.

In the flame retardant resin composition, it is preferable that the average particle diameter of the calcium carbonate particles be 1.2 μm or more.

In this case, more excellent flame retardancy is obtained compared to a case in which the average particle diameter of the calcium carbonate particles is less than 1.2 μm.

In the flame retardant resin composition, it is preferable that the average particle diameter of the calcium carbonate particles be 8.0 μm or less.

In this case, more excellent mechanical characteristics can be obtained compared to a case in which the average particle diameter of the calcium carbonate particles is 8.0 μm or more.

In the flame retardant resin composition, it is preferable that the fatty acid-containing compound be formed of at least one selected from the group consisting of magnesium stearate and calcium stearate.

In this case, more excellent flame retardancy is obtained compared to a case in which the fatty acid-containing compound is none of magnesium stearate and calcium stearate.

In the flame retardant resin composition, it is preferable that the zinc-containing inorganic compound be formed of at least one selected from the group consisting of zinc hydroxystannate and zinc borate.

In this case, more excellent flame retardancy is obtained compared to a case in which the zinc-containing inorganic compound is none of zinc hydroxystannate and zinc borate.

In the flame retardant resin composition, it is preferable that the zinc-containing inorganic compound be blended at a ratio of 5 parts by mass or less relative to 100 parts of the polyolefin resin.

In this case, more excellent flame retardancy can be obtained.

In the flame retardant resin composition, it is preferable that the blending ratio of calcium carbonate particles and aluminum hydroxide be 55 parts by mass or more and 100 parts by mass or less in total relative to 100 parts by mass of the polyolefin resin.

In this case, both more excellent flame retardancy and mechanical characteristics can be realized.

In addition, the present invention is a cable comprising an insulated wire, in which the insulated wire has a conductor and an insulating layer covering the conductor, and the insulating layer is formed of the above-mentioned flame retardant resin composition.

Furthermore, the present invention is a cable having a conductor, an insulating layer covering the conductor, and a sheath covering the insulating layer, in which at least one of the insulating layer and the sheath is formed of the above-mentioned flame retardant resin composition.

Furthermore, the present invention is an optical fiber cable comprising an optical fiber and an insulating layer covering the optical fiber, in which the insulating layer is formed of the above-mentioned flame retardant resin composition.

Incidentally, in the present invention, the term "average particle diameter" refers to the average value of R, which is obtained by, when plural calcium carbonate particles are observed by scanning electron microscope (SEM), determining the two-dimensional image area S of each particle, considering each of these values of S as being equal to the area of a circle and calculating R of each particle based on the following formula:

$$R = 2 \times (S/\pi)^{1/2}.$$

Effect of the Invention

According to the present invention, a flame retardant resin composition which can secure more excellent flame retardancy while securing excellent mechanical characteristics, and a cable and an optical fiber cable using the same are provided.

MODE(S) FOR CARRYING OUT THE INVENTION

Hereinbelow, embodiments of the invention are described in detail using FIG. 1 to FIG. 3.

[Cable]

Figure 1:
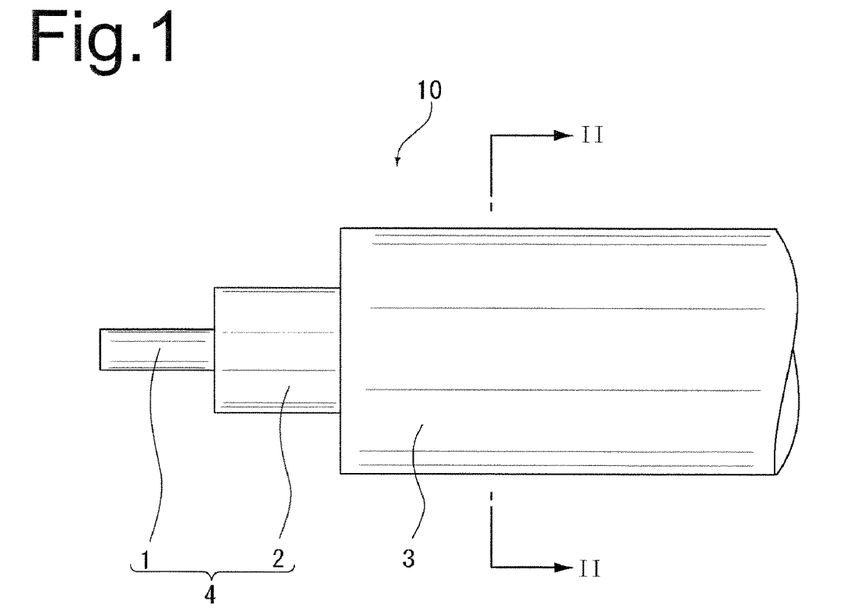
FIG. 1 is a partial side view illustrating one embodiment of the cable of the present invention.
Figure 2:
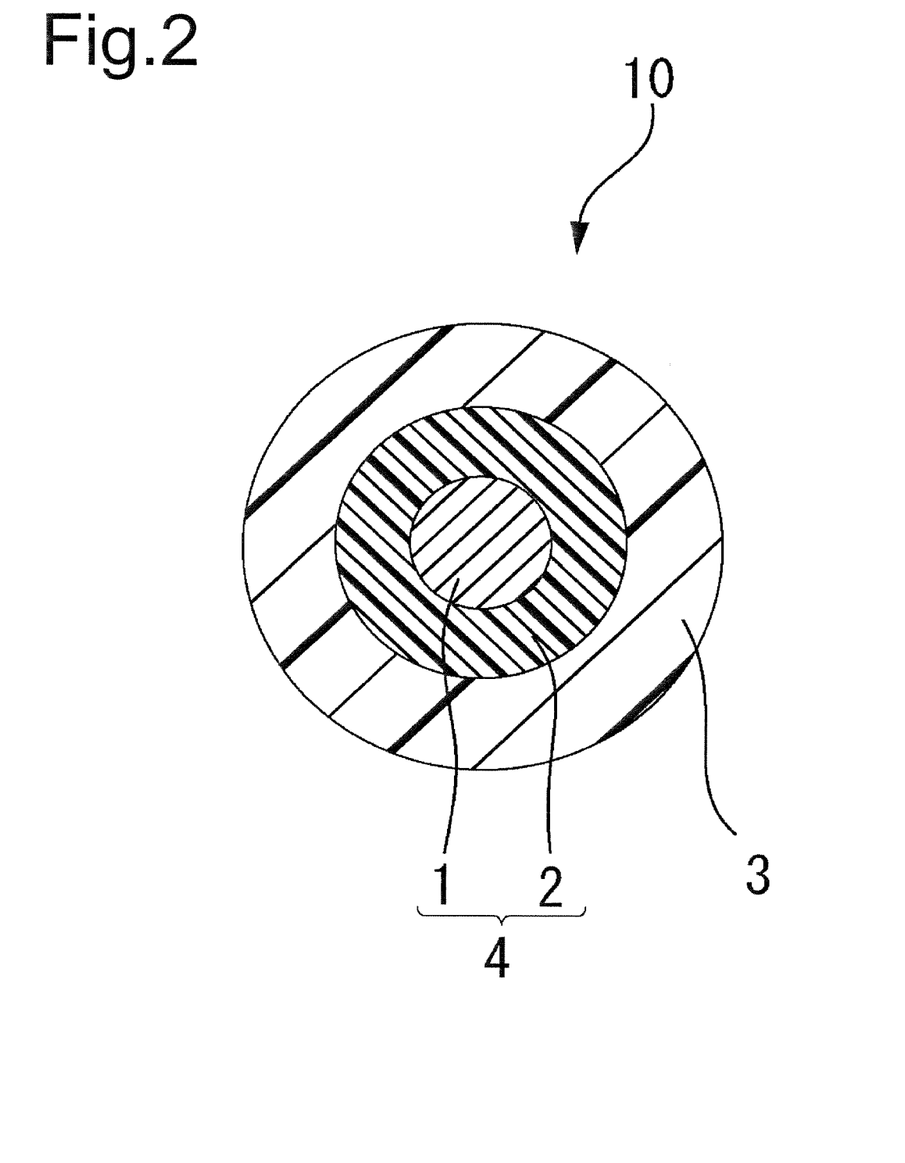
FIG. 2 is a cross-sectional view taken along the line II-II of FIG. 1.

FIG. 1 is a partial side view illustrating one embodiment of the cable according to the present invention, and FIG. 2 is a cross-sectional view taken along the line II-II of FIG. 1. As shown in FIG. 1 and FIG. 2, a cable 10 is provided with one insulated wire 4 and a sheath 3 covering the insulated wire 4. Furthermore, the insulated wire 4 has an internal conductor 1 and an insulating layer 2 covering the internal conductor 1.

[Optical Fiber Cable]

Figure 3:
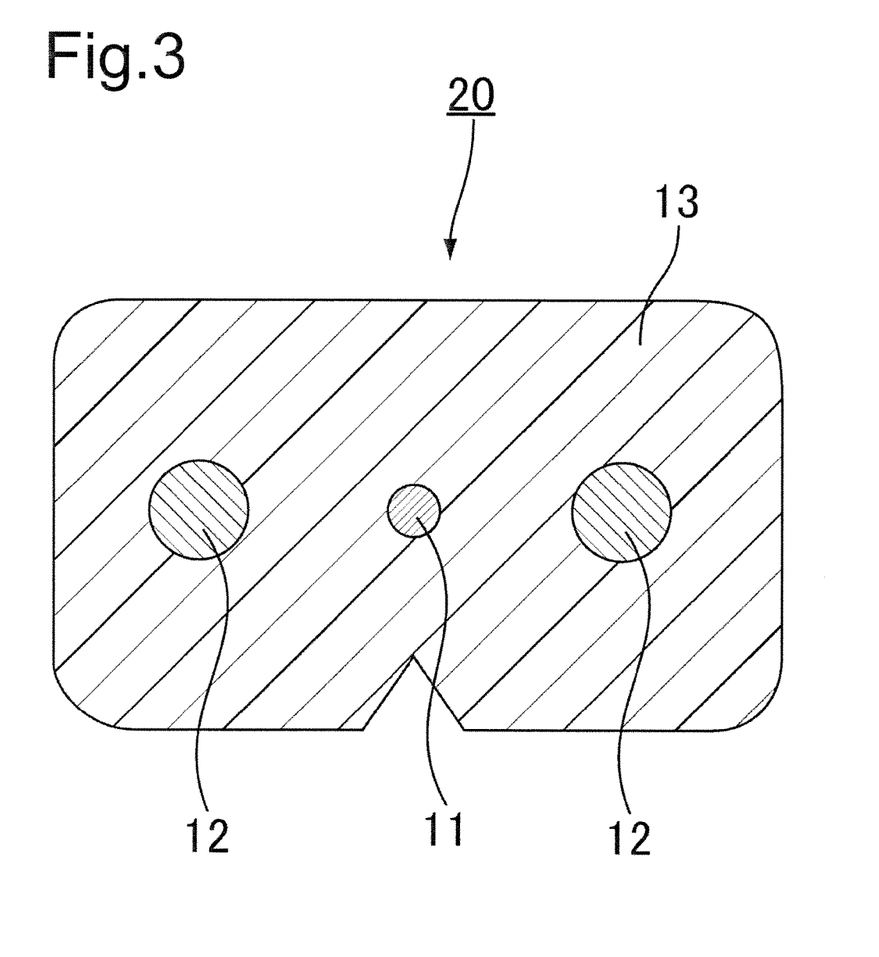
FIG. 3 is a cross-sectional view illustrating one embodiment of the optical fiber cable of the present invention.

FIG. 3 is a cross-sectional view illustrating an indoor type optical fiber cable which is one embodiment of an optical fiber cable according to the present invention. As shown in FIG. 3, an optical fiber cable 20 has one optical fiber 11, two tension members 12, and a sheath 13 as an insulating layer covering the optical fiber 11 and the tension members 12. Incidentally, the tension member is formed of a material with high tensile strength such as steel wire.

Herein, the insulating layer 2 and the sheaths 3 and 13 are formed of a flame retardant resin composition, and this flame retardant resin composition has a polyolefin resin, calcium carbonate particles blended at a ratio of 5 parts by mass or more and 80 parts by mass or less relative to 100 parts by mass of the polyolefin resin, aluminum hydroxide blended at a ratio of 50 parts by mass or more and 125 parts by mass or less relative to 100 parts by mass of the polyolefin resin, a silicone-based compound blended at a ratio of more than 1 part by mass and 10 parts by mass or less relative to 100 parts by mass of the polyolefin resin, a fatty acid-containing compound blended at a ratio of 3 parts by mass or more and 20 parts by mass or less relative to 100 parts by mass of the polyolefin resin, and a zinc-containing inorganic compound blended at a ratio of 1 part by mass or more and 7 parts by mass or less relative to 100 parts by mass of the polyolefin resin, in which a total of the calcium carbonate particles and aluminum hydroxide is 55 parts by mass or more and 130 parts by mass or less relative to 100 parts by mass of the polyolefin resin.

The above-mentioned flame retardant resin composition can secure more excellent flame retardancy while securing excellent mechanical characteristics. For this reason, the insulating layer 2 and the sheaths 3 and 13 that are formed of the above-mentioned flame retardant resin composition can secure more excellent flame retardancy while securing excellent mechanical characteristics. For this reason, the cable 10 and the optical fiber cable 20 can secure more excellent flame retardancy while securing excellent mechanical characteristics.

[Method for Producing Cable]

Next, a method for producing the above-mentioned cable 10 is described.

(Conductor)

First, the internal conductor 1 is prepared. The internal conductor 1 may be formed of a single wire, or may be composed of plural wires that are bundled together. Furthermore, the internal conductor 1 is not particularly limited on the diameter of the conductor, the material of the conductor and the like, which can be appropriately determined according to the use.

(Flame Retardant Resin Composition)

On the other hand, the above-mentioned flame retardant resin composition is prepared. As described above, the flame retardant resin composition has a polyolefin resin, calcium carbonate particles blended at a ratio of 5 parts by mass or more and 80 parts by mass or less relative to 100 parts by mass of the polyolefin resin, aluminum hydroxide blended at a ratio of 50 parts by mass or more and 125 parts by mass or less, a silicone-based compound blended at a ratio of more than 1 part by mass and 10 parts by mass or less relative to 100 parts by mass of the polyolefin resin, a fatty acid-containing compound blended at a ratio of 3 parts by mass or more and 20 parts by mass or less relative to 100 parts by mass of the polyolefin resin, and a zinc-containing inorganic compound blended at a ratio of 1 part by mass or more and 7 parts by mass or less relative to 100 parts by mass of the polyolefin resin, in which a total of the calcium carbonate particles and aluminum hydroxide is 55 parts by mass or more and 130 parts by mass or less relative to 100 parts by mass of the polyolefin resin.

(Polyolefin Resin)

Examples of the polyolefin resin include an ethylene-based resin and a propylene-based resin. These may be used either singly or as a mixture of two or more thereof. Herein, the ethylene-based resin refers to a resin which contains ethylene as a constitutional unit and examples of the ethylene-based resin include a polyethylene resin (PE), an ethylene ethyl acrylate copolymer (EEA), and an ethylene vinyl acetate copolymer (EVA). Furthermore, the propylene-based resin refers to a resin which contains propylene as a constitutional unit and examples of the propylene-based resin include a polypropylene resin (PP).

(Calcium Carbonate Particles)

The calcium carbonate particles may be any one of heavy calcium carbonate and light calcium carbonate. The average particle diameter of the calcium carbonate particles is preferably 1.2 μm or more as described above. In this case, excellent flame retardancy can be obtained compared to a case in which the average particle diameter of the calcium carbonate particles is less than 1.2 μm. The average particle diameter of the calcium carbonate particles is more preferably 1.5 μm or more. Furthermore, the average particle diameter of the calcium carbonate particles is preferably 8.0 μm or less. In this case, more excellent mechanical characteristics can be obtained compared to a case in which the average particle diameter of the calcium carbonate particles is 8.0 μm or more. The average particle diameter of the calcium carbonate particles is preferably 5.0 μm or less, more preferably 3.0 μm or less, and particularly preferably 2.0 μm or less.

The calcium carbonate particles are blended at a ratio of 5 parts by mass or more and 80 parts by mass or less relative to 100 parts by mass of the polyolefin resin. In this case, excellent flame retardancy can be obtained compared to a case in which blending ratio of the calcium carbonate particles is less than 5 parts by mass relative to 100 parts by mass of the polyolefin resin. The blending ratio of the calcium carbonate particles is preferably 10 parts by mass or more, more preferably 30 parts by mass or more, and particularly preferably 40 parts by mass or more relative to 100 parts by mass of the polyolefin resin. However, the blending ratio of the calcium carbonate particles is preferably 70 parts by mass or less, and more preferably 50 parts by mass or less relative to 100 parts by mass of the polyolefin resin.

(Aluminum Hydroxide)

Aluminum hydroxide is not particularly limited as long as it can be dispersed in the polyolefin resin. The aluminum hydroxide is blended at a ratio of 50 parts by mass or more and 125 parts by mass or less relative to 100 parts by mass of the polyolefin resin. In this case, excellent flame retardancy can be obtained compared to a case in which the blending ratio of the aluminum hydroxide is less than 50 parts by mass relative to 100 parts by mass of the polyolefin resin. The blending ratio of the aluminum hydroxide is preferably 60 parts by mass or more relative to 100 parts by mass of the polyolefin resin. However, the blending ratio of the aluminum hydroxide is preferably 90 parts by mass or less relative to 100 parts by mass of the polyolefin resin.

Herein, the total blending ratio of the calcium carbonate particles and aluminum hydroxide particles is 55 parts by mass or more and 130 parts by mass or less relative to 100 parts by mass of the polyolefin resin. In this case, excellent flame retardancy can be obtained compared to a case in which the total blending ratio of the calcium carbonate particles and aluminum hydroxide is less than 55 parts by mass relative to 100 parts by mass of the polyolefin resin. On the other hand, more excellent mechanical characteristics can be obtained compared to a case in which the total blending ratio of the calcium carbonate particles and aluminum hydroxide is more than 130 parts by mass relative to 100 parts by mass of the polyolefin resin.

Furthermore, the total blending ratio of the calcium carbonate particles and aluminum hydroxide is 55 parts by mass or more and 100 parts by mass or less relative to 100 parts by mass of the polyolefin resin. In this case, both more excellent flame retardancy and mechanical characteristics can be realized. The total blending ratio of the calcium carbonate particles and aluminum hydroxide is preferably 60 parts by mass or more relative to 100 parts by mass of the polyolefin resin. However, the total blending ratio of the calcium carbonate particles and aluminum hydroxide is preferably 90 parts by mass or less relative to 100 parts by mass of the polyolefin resin.

(Silicone-Based Compound)

The silicone-based compound functions as a flame retardant aid. Examples of the silicone-based compound include polyorganosiloxanes. Herein, the polyorganosiloxanes are compounds which have siloxane bonds as a main chain, and have organic groups in side chains. Examples of the organic groups include a methyl group, a vinyl group, an ethyl group, a propyl group, and a phenyl group. Specific examples of the polyorganosiloxanes include dimethylpolysiloxane, methylethylpolysiloxane, methyloctylpolysiloxane, methylvinylpolysiloxane, methylphenylpolysiloxane, and methyl-(3,3,3-trifluoropropyl)polysiloxane. Examples of polyorganosiloxane include silicone powders, silicone gum, and silicone resin. Among them, silicone gum is preferable. In this case, blooming is unlikely to occur.

As described above, the silicone-based compound is blended at a ratio of more than 1 part by mass and 10 parts by mass or less relative to 100 parts by mass of the polyolefin resin. In this case, excellent flame retardancy can be obtained compared to a case in which the blending ratio of the silicone-based compound is 1 part by mass or less relative to 100 parts by mass of the polyolefin resin. On the other hand, compared to a case in which the blending ratio of the silicone-based compound is more than 10 parts by mass relative to 100 parts by mass of the polyolefin resin, blooming is unlikely to occur. The blending ratio of the silicone-based compound is preferably 2 parts by mass or more relative to 100 parts by mass of the polyolefin resin. However, the blending ratio of the silicone-based compound is preferably 8 parts by mass or less, and more preferably 5 parts by mass or less relative to 100 parts by mass of the polyolefin resin.

The silicone-based compound may be attached in advance to the surface of the calcium carbonate particles. In this case, it is preferable that the entirety of each of the calcium carbonate particles included in the flame retardant resin composition be covered with the silicone-based compound. In this case, since the calcium carbonate particles can be easily dispersed in the polyolefin resin, uniformity of the characteristics in the flame retardant resin composition is further improved. In addition, it is possible to suppress bleed-out of the silicone-based compound at the time of extrusion processing of the flame retardant resin composition.

Examples of the method of attaching the silicone-based compound to the surface of the calcium carbonate particles include, for example, a method in which the silicone-based compound is added to calcium carbonate, they are mixed to obtain a mixture, the mixture is then dried at 40° C. to 75° C. for 10 minutes to 40 minutes, and the dried mixture is pulverized with a Henschel mixer, an atomizer or the like.

(Fatty Acid-Containing Compound)

The fatty acid-containing compound is a compound which functions as a flame retardant aid. The fatty acid-containing compound refers to a fatty acid or a compound containing a metal salt thereof. As the fatty acid, for example, a fatty acid having 12 to 28 carbon atoms is used. Examples of such a fatty acid include lauric acid, myristic acid, palmitic acid, stearic acid, tuberculostearic acid, oleic acid, linoleic acid, arachidonic acid, behenic acid, and montanic acid. Among them, the fatty acid is preferably stearic acid or tuberculostearic acid. Stearic acid is particularly preferred. In this case, more excellent flame retardancy is obtained compared to a case in which a fatty acid other than stearic acid or tuberculostearic acid is used.

Examples of the metal that constitutes a metal salt of the fatty acid include magnesium, calcium, zinc, and lead. The metal salt of the fatty acid is preferably magnesium stearate, calcium stearate, or a mixture thereof. In this case, more excellent flame retardancy is obtained.

As described above, the fatty acid-containing compound is blended at a ratio of 3 parts by mass or more and 20 parts by mass or less relative to 100 parts by mass of the polyolefin resin.

In this case, excellent flame retardancy can be obtained compared to a case in which the blending ratio of the fatty acid-containing compound is less than 3 parts by mass relative to 100 parts by mass of the polyolefin resin. On the other hand, compared to a case in which the blending ratio of the silicone-based compound is more than 20 parts by mass relative to 100 parts by mass of the polyolefin resin, blooming is unlikely to occur. The blending ratio of the fatty acid-containing compound is preferably 5 parts by mass or more, and more preferably 7 parts by mass or more relative to 100 parts by mass of the polyolefin resin. However, the blending ratio of the fatty acid-containing compound is preferably 15 parts by mass or less, and more preferably 10 parts by mass or less relative to 100 parts by mass of the polyolefin resin.

(Zinc-Containing Inorganic Compound)

The zinc-containing inorganic compound is an inorganic compound which contains at least zinc. Examples of the zinc-containing inorganic compound include zinc borate, zinc stannate, and zinc hydroxystannate. Among them, as the zinc-containing inorganic compound, zinc borate, zinc hydroxystannate, or a mixture thereof is preferable. In this case, more excellent flame retardancy is obtained compared to a case in which a zinc-containing inorganic compound other than zinc borate and zinc hydroxystannate is used.

The zinc-containing inorganic compound is blended at a ratio of 1 part by mass or more and 7 parts by mass or less relative to 100 parts by mass of the polyolefin resin.

In this case, as the blending ratio of the zinc-containing inorganic compound relative to 100 parts by mass of the polyolefin resin is within the above range, the flame retardancy is significantly improved compared to a case in which the blending ratio of the zinc-containing inorganic compound is less than 1 part by mass. On the other hand, compared to a case in which the blending ratio of the zinc-containing inorganic compound is more than 7 parts by mass relative to 100 parts by mass of the polyolefin resin, the flame retardancy is significantly improved.

The blending ratio of the zinc-containing inorganic compound is preferably 7 parts by mass or less relative to 100 parts by mass of the polyolefin resin. The blending ratio of the zinc-containing inorganic compound is more preferably 5 parts by mass or less relative to 100 parts by mass of the polyolefin resin. In this case, more excellent flame retardancy can be obtained. However, the blending ratio of the zinc-containing inorganic compound is preferably 3 parts by mass or more relative to 100 parts by mass of the polyolefin resin.

The above-mentioned flame retardant resin composition may also contain an oxidation inhibitor, an ultraviolet ray deterioration inhibitor, a processing aid, a coloring pigment, a lubricating agent, and a filler such as carbon black as necessary.

The above-mentioned flame retardant resin composition can be obtained by kneading the polyolefin resin, calcium carbonate, aluminum hydroxide, the silicone-based compound, the fatty acid-containing compound, and the zinc-containing inorganic compound. Kneading can be carried out with, for example, a kneading device such as a Banbury mixer, a tumbler, a pressurized kneader, a kneader extruder, a twin screw extruder, a mixing roll or the like. At this time, from the viewpoint of improving the dispersion property of the silicone-based compound, a master batch (MB) obtained by kneading a portion of the polyolefin resin and the silicone-based compound may be kneaded with the remaining polyolefin resin, calcium carbonate, a fatty acid or metal salt of a fatty acid, and a monoester compound of a polyhydric alcohol and a fatty acid, or the like.

Next, the internal conductor 1 is covered with the above-mentioned flame retardant resin composition. Specifically, the flame retardant resin composition described above is melt-kneaded by using an extruder, and a tube-shaped extrusion product is formed. Then, this tube-shaped extrusion product is continuously covered on the internal conductor 1. Thus, the insulated wire 4 is obtained.

(Sheath)

Finally, one insulated wire 4 obtained as described above is prepared, and this insulated wire 4 is covered with the sheath 3 which has been produced by using the flame retardant resin composition described above. The sheath 3 protects the insulating layer 2 from physical or chemical damage.

In the above manner, the cable 10 is obtained.

The cable of the present invention is not limited to the cable 10 of the embodiment described above. For example, in the above embodiment, the cable 10 has one insulated wire 4. However, the cable of the present invention is not limited to a cable which has one insulated wire 4, and the cable may have two or more insulated wires 4 on the inner side of the sheath 3. Furthermore, a resin section formed of polypropylene or the like may also be provided between the sheath 3 and the insulated wire 4.

Furthermore, in the above embodiment, the insulating layer 2 and the sheath 3 of the insulated wire 4 are formed of the above-mentioned flame retardant resin composition, but it is also possible that the insulating layer 2 is formed of a typical insulating resin, and only the sheath 3 is formed of the above-mentioned flame retardant resin composition. Namely, it is possible that only the sheath 3 is formed of the above-mentioned flame retardant resin composition, and the insulating layer 2 is not formed of the above-mentioned flame retardant resin composition.

[Method for Producing Optical Fiber Cable]

In addition, explanations are given for the method for producing the optical fiber cable 20 described above.

First, an optical fiber 11, tension members 12 and the above-mentioned flame retardant resin composition are prepared.

Next, the optical fiber 11 and the tension members 12 are covered with the above-mentioned flame retardant resin composition. Specifically, the above-mentioned flame retardant resin composition is melt-kneaded by using an extruder. Then, on the optical fiber 11 and the tension members 12 that are arranged as shown in FIG. 3, a tube-shaped extrusion product having a cross-section shape shown in FIG. 3 is extruded from the extruder so that the tube-shaped extrusion product continuously covers the optical fiber 11 and the tension members 12. Thus, the optical fiber cable 20 is obtained.

The optical fiber cable of the present invention is not limited to the optical fiber cable 20 of the above embodiment. As long as the flame retardant resin composition can be applied, the optical fiber cable may be an optical fiber cable of any type.

EXAMPLES

Hereinbelow, the contents of the present invention are more specifically described by way of Examples and Comparative Examples, but the present invention is not limited to the following Examples.

Examples 1 to 12 and Comparative Examples 1 to 8

A polyolefin resin, calcium carbonate particles, aluminum hydroxide, a silicone-based compound (silicone MB), a fatty acid-containing compound, a zinc-containing inorganic compound, and an inorganic compound were blended with a blending amount shown in Table 1 to Table 4, were kneaded for 15 minutes at 160° C. using a Banbury mixer, and a flame retardant resin composition was thus obtained. Incidentally, in Table 1 to Table 4, the unit of the blending amount of each blending component is part(s) by mass. Furthermore, in Table 1 to Table 4, although the blending amount of the polyolefin resin is not 100 parts by mass, the resin is also included in the silicone MB. Accordingly, when the blending amount of the polyolefin resin and the blending amount of the resin in the silicone MB are added, the total amount of the polyolefin resin becomes 100 parts by mass.

As the above-mentioned polyolefin resin, calcium carbonate particles, aluminum hydroxide, the silicone-based compound, the fatty acid-containing compound, the zinc-containing inorganic compound, and the inorganic compound, those described below were specifically used.

(1) Polyolefin Resin

Polyethylene resin (PE) (trade name: "EXCELLEN GMHGH030", manufactured by Sumitomo Chemical Company, Limited)

(2) Calcium Carbonate Particles

Calcium carbonate particles (average particle diameter of 1.7 μm) (trade name: "NCC-P", manufactured by Nitto Funka Kogyo K.K.)

(3) Aluminum Hydroxide

Aluminum hydroxide (trade name: "BF013S", manufactured by Nippon Light Metal Company, Ltd.)

(4) Silicone-Based Compound

Silicone MB (trade name: "X-22-2125H", manufactured by Shin-Etsu Chemical Co., Ltd., containing 50% by mass of silicone gum and 50% by mass of PE)

(5) Fatty Acid-Containing Compound

Magnesium stearate (Mg stearate) (trade name: "AFCO CHEM MGS", manufactured by ADEKA CORPORATION)

(6) Zinc-Containing Inorganic Compound (A) Zinc hydroxystannate (trade name: "Flamtard H", manufactured by Nippon Light Metal Company, Ltd.)

(B) Zinc borate (trade name: "Alcanex FRC500", manufactured by MIZUSAWA INDUSTRIAL CHEMICALS, LTD.)

(7) Inorganic Compound

Antimony trioxide (manufactured by NIHON SEIKO CO., LTD.)

Subsequently, the flame retardant resin composition was kneaded for 15 minutes at 160° C. with a Banbury mixer. Thereafter, this flame retardant resin composition was fed into a single screw extruder (L/D=20, shape of screw: full flight screw, manufactured by Marth Seiki Co., Ltd.), and a tube-shaped extrusion product was extruded from the extruder and covered a conductor (number of single wires: one/cross-sectional area: 2 mm$^2$) to have a thickness of 0.7 mm. Thus, an insulated wire was obtained.

TABLE 1

| | | | Example 1 | Example 2 | Example 3 | Example 4 | Example 5 | Comparative Example 1 | Comparative Example 2 | Comparative Example 3 |
|---|---|---|---|---|---|---|---|---|---|---|
| Resin composition | Polyolefin resin | PE | 95 | 95 | 95 | 95 | 95 | 95 | 95 | 95 |
| | Calcium carbonate particles | | 40 | 40 | 40 | 5 | 80 | | 80 | 40 |
| | Aluminum hydroxide | | 50 | 60 | 90 | 50 | 50 | 50 | 40 | 120 |
| | Silicone-based compound | Silicone MB (PE/Silicone gum) | 5/5 | 5/5 | 5/5 | 5/5 | 5/5 | 5/5 | 5/5 | 5/5 |
| | Fatty acid-containing compound | Mg stearate | 10 | 10 | 10 | 10 | 10 | 10 | 10 | 10 |
| | Zinc-containing inorganic compound | Zinc hydroxystannate | 1 | 1 | 1 | 1 | 1 | 1 | 1 | 1 |

TABLE 1-continued

|  |  |  | Example 1 | Example 2 | Example 3 | Example 4 | Example 5 | Comparative Example 1 | Comparative Example 2 | Comparative Example 3 |
|---|---|---|---|---|---|---|---|---|---|---|
| Flame retardancy | Vertical test for single wire | Pass rate % | 100 | 100 | 100 | 100 | 100 | 100 | 100 | 100 |
|  | Vertical test for three wires | Pass rate % | 90 | 100 | 100 | 100 | 100 | 60 | 0 | 100 |
|  | Mechanical characteristics (MPa) |  | 11.6 | 11 | 10.2 | 12.1 | 10.3 | 12 | 10.6 | 8.6 |

TABLE 2

|  |  |  | Comparative Example 4 | Example 6 | Comparative Example 5 | Example 7 |
|---|---|---|---|---|---|---|
| Resin composition | Polyolefin resin | PE | 99 | 98 | 95 | 95 |
|  | Calcium carbonate particles |  | 40 | 40 | 40 | 40 |
|  | Aluminum hydroxide |  | 60 | 60 | 60 | 60 |
|  | Silicone-based compound | Silicone MB (PE/Silicone gum) | 1/1 | 2/2 | 5/5 | 5/5 |
|  | Fatty acid-containing compound | Mg stearate | 10 | 10 |  | 3 |
|  | Zinc-containing inorganic compound | Zinc hydroxystannate | 1 | 1 | 1 | 1 |
| Flame retardancy | Vertical test for single wire | Pass rate % | 0 | 100 | 0 | 100 |
|  | Vertical test for three wires | Pass rate % | 0 | 90 | 0 | 100 |
|  | Mechanical characteristics (MPa) |  | 11.2 | 10.8 | 11.6 | 11.5 |

TABLE 3

|  |  |  | Comparative Example 6 | Example 8 | Example 9 | Example 10 | Example 11 | Comparative Example 7 |
|---|---|---|---|---|---|---|---|---|
| Resin composition | Polyolefin resin | PE | 95 | 95 | 95 | 95 | 95 | 95 |
|  | Calcium carbonate particles |  | 40 | 40 | 40 | 40 | 40 | 40 |
|  | Aluminum hydroxide |  | 60 | 60 | 60 | 60 | 60 | 60 |
|  | Silicone-based compound | Silicone MB (PE/Silicone gum) | 5/5 | 5/5 | 5/5 | 5/5 | 5/5 | 5/5 |
|  | Fatty acid-containing compound | Mg stearate | 10 | 10 | 10 | 10 | 10 | 10 |
|  | Zinc-containing inorganic compound | Zinc hydroxystannate |  | 1 | 3 | 5 | 7 | 10 |
| Flame retardancy | Vertical test for single wire | Pass rate % | 100 | 100 | 100 | 100 | 100 | 100 |
|  | Vertical test for three wires | Pass rate % | 60 | 100 | 100 | 100 | 90 | 60 |
|  | Mechanical characteristics (MPa) |  | 11.2 | 11.6 | 11.4 | 11.1 | 11 | 10.8 |

TABLE 4

|  |  |  | Example 12 | Comparative Example 8 |
|---|---|---|---|---|
| Resin composition | Polyolefin resin | PE | 95 | 95 |
|  | Calcium carbonate particles |  | 40 | 40 |
|  | Aluminum hydroxide |  | 60 | 60 |
|  | Silicone-based compound | Silicone MB (PE/Silicone gum) | 5/5 | 5/5 |
|  | Fatty acid-containing compound | Mg stearate | 10 | 10 |
|  | Zinc-containing inorganic compound | Zinc borate | 3 |  |
|  | Inorganic compound | Antimony trioxide |  | 3 |
| Flame retardancy | Vertical test for single wire | Pass rate % | 100 | 0 |
|  | Vertical test for three wires | Pass rate % | 100 | 0 |
|  | Mechanical characteristics (MPa) |  | 11.4 | 11.6 |

For the insulated wires of Examples 1 to 12 and Comparative Examples 1 to 8 which have been obtained as described above, evaluation of the flame retardancy and mechanical characteristics was carried out as described below.

<Flame Retardancy>

As for the flame retardancy, if the insulated wires of Examples 1 to 12 and Comparative Examples 1 to 8 pass both the vertical test for a single wire and the vertical test for three wires, they were considered as having excellent flame retardancy and graded as "pass." If they do not pass at least one of the vertical test for a single wire and the vertical test for three wires, they were considered as having no excellent flame retardancy and graded as "failure."

(Vertical Test for Single Wire)

Ten insulated wires were prepared for each of Examples 1 to 12 and Comparative Examples 1 to 8. Then, a vertical combustion test for a single wire was performed for those wires based on JIS C3665-1. At this time, specifically, an insulating wire with the length of "50 mm or more" or "540 mm or less" between the lower end of the upper supporting member, which supports the insulated wire at the top, and the end point of carbonization was graded as "pass", and an insulated wire with the length less than 50 mm or more than 540 mm was graded as "failure." Then, the pass rate (%) was calculated. The results are shown in Table 1 to Table 4. In Table 1 to Table 4, the combustion time was also shown. Furthermore, in Table 1 to Table 4, the criteria for the pass or failure in the vertical test for a single wire were as follows. Incidentally, in the combustion test, the insulated wire was brought into contact with burner flame for 60 seconds.

Pass rate of 70% or more: pass
Pass rate of less than 70%: failure (Vertical Test for Three Wires)

Fifteen insulated wires were prepared for each of Examples 1 to 12 and Comparative Examples 1 to 8, and a vertical combustion test for three wires was carried out for them. Specifically, the insulated wires with the length of 550 mm were vertically hung, each in a set of three wires, at equal intervals. The interval between the insulated wires was set to a distance that was 2 times the diameter of the insulated wire. For Examples 1 to 12 and Comparative Examples 1 to 8, the interval was set to 8 mm. By using a bunsen burner, the insulated wires were brought into contact with flame such that the distance between the burner opening and the lower ends of the insulated wires was 40 mm and flame with the length of 150 mm formed an angle of 45°. Then, the flame contact was continued until the insulated wires were self extinguished or completely combusted. The insulated wire showing self extinguishment was graded as "pass" while the completely combusted insulated wire was graded as "failure." Then, the operation of vertically hanging the insulated wires, each in a set of three wires, at equal intervals followed by carrying out the flame contact was repeated 5 times, and the pass rate (%) was calculated. The results are shown in Table 1 to Table 4. In Table 1 to Table 4, the criteria for the pass or failure in the vertical test for three wires were as follows.

Pass rate of 70% or more: pass
Pass rate of less than 70%: failure

<Mechanical Characteristics>

The evaluation of the mechanical characteristics for the insulated wires of Examples 1 to 12 and Comparative Examples 1 to 8 was performed based on the tensile strength that is measured by tensile test according to JIS C3005. The results are shown in Tables 1 to 4. In Tables 1 to 4, the unit of the tensile strength is MPa, and the criteria for the pass or failure in terms of the tensile strength was as follows. In the tensile test, the elongation rate was 200 mm/min and the gauge length was 20 mm.

10 MPa or more: Pass
Less than 10 MPa: Failure

From the results shown in Table 1 to Table 4, the insulated wires of Examples 1 to 12 reached the pass criteria for the flame retardancy and mechanical characteristics. In contrast, the insulated wires of Comparative Examples 1 to 8 did not reach at least one of the pass criteria for the flame retardancy and mechanical characteristics.

From this point of view, it was confirmed that, according to the flame retardant resin composition of the present invention, more excellent flame retardancy can be secured while excellent mechanical characteristics are secured.

EXPLANATIONS OF REFERENCE NUMERALS

1 . . . Internal conductor
2 . . . Insulating layer
3 . . . Sheath
4 . . . Insulated wire
10 . . . Cable
11 . . . Optical fiber
12 . . . Tension member
13 . . . Sheath
20 . . . Optical fiber cable

The invention claimed is:

1. A flame retardant resin composition comprising:
 a polyolefin resin;
 calcium carbonate particles blended at a ratio of 5 parts by mass or more and 80 parts by mass or less relative to 100 parts by mass of the polyolefin resin;
 aluminum hydroxide blended at a ratio of 50 parts by mass or more and 125 parts by mass or less relative to 100 parts by mass of the polyolefin resin;
 a silicone-based compound blended at a ratio of more than 1 part by mass and 10 parts by mass or less relative to 100 parts by mass of the polyolefin resin;
 a fatty acid-containing compound blended at a ratio of 3 parts by mass or more and 20 parts by mass or less relative to 100 parts by mass of the polyolefin resin; and
 a zinc-containing inorganic compound blended at a ratio of 1 part by mass or more and 7 parts by mass or less relative to 100 parts by mass of the polyolefin resin,
 wherein the calcium carbonate particles and the aluminum hydroxide are blended in total at a ratio of 55 parts by mass or more and 130 parts by mass or less relative to 100 parts by mass of the polyolefin resin.

2. The flame retardant resin composition according to claim 1,
 wherein the average particle diameter of the calcium carbonate particles is 1.2 µm or more.

3. The flame retardant resin composition according to claim 1,
 wherein the average particle diameter of the calcium carbonate particles is 8.0 µm or less.

4. The flame retardant resin composition according to claim 1,
 wherein the fatty acid-containing compound is formed of at least one selected from the group consisting of magnesium stearate and calcium stearate.

5. The flame retardant resin composition according to claim 1,
 wherein the zinc-containing inorganic compound is formed of at least one selected from the group consisting of zinc hydroxystannate and zinc borate.

6. The flame retardant resin composition according to claim 5, wherein the zinc-containing inorganic compound is zinc hydroxystannate.

7. The flame retardant resin composition according to claim 1,
wherein the zinc-containing inorganic compound is blended at a ratio of 5 parts by mass or less relative to 100 parts by mass of the polyolefin resin.

8. The flame retardant resin composition according to claim 1,
wherein the blending ratio of the calcium carbonate particles and the aluminum hydroxide is 55 parts by mass or more and 100 parts by mass or less in total relative to 100 parts by mass of the polyolefin resin.

9. A cable comprising an insulated wire,
wherein the insulated wire has a conductor and an insulating layer covering the conductor, and
the insulating layer is formed of the flame retardant resin composition according to claim 1.

10. A cable comprising:
a conductor;
an insulating layer covering the conductor; and
a sheath covering the insulating layer,
wherein at least one of the insulating layer and the sheath is formed of the flame retardant resin composition according to claim 1.

11. An optical fiber cable comprising:
an optical fiber; and
an insulating layer covering the optical fiber,
wherein the insulating layer is formed of the flame retardant resin composition according to claim 1.

12. The flame retardant resin composition according to claim 1, wherein the blending ratio of the zinc-containing inorganic compound is 1 part by mass or more and 3 parts by mass or less relative to 100 parts by mass of the polyolefin resin.

13. The flame retardant resin composition according to claim 1, wherein the blending ratio of the fatty acid-containing compound is 5 parts by mass or more and 20 parts by mass or less relative to 100 parts by mass of the polyolefin resin.

14. The flame retardant resin composition according to claim 1, wherein a ratio of the blending ratio of the calcium carbonate to the blending ratio of the aluminum hydroxide is 0.67 or less.

* * * * *